United States Patent [19]
Schultz

[11] Patent Number: 5,562,077
[45] Date of Patent: Oct. 8, 1996

[54] METHOD AND APPARATUS FOR VENTILATION AND ASPIRATION

[76] Inventor: Joseph Schultz, 564 First Ave., Apt. 21-R, New York, N.Y. 10016

[21] Appl. No.: 416,304

[22] Filed: Apr. 4, 1995

[51] Int. Cl.[6] .................. A61M 16/04; A61M 25/088
[52] U.S. Cl. ................ 128/207.14; 128/202.27; 604/35
[58] Field of Search .............. 128/200.24, 202.27, 128/207.14, 207.15, 207.16, 200.26, 204.18, 205.19; 604/35

[56] References Cited

U.S. PATENT DOCUMENTS

| | | | |
|---|---|---|---|
| 4,193,406 | 3/1980 | Jinotti | 128/204.18 |
| 4,275,724 | 6/1981 | Behrstock | 128/207.14 |
| 4,487,600 | 12/1984 | Brownie et al. | 604/35 |
| 4,534,542 | 8/1985 | Russo | 251/342 |
| 4,699,138 | 10/1987 | Behrstock | 128/207.16 |
| 4,787,894 | 11/1988 | Turnbull | 604/319 |
| 4,805,611 | 2/1989 | Hodgkins | 128/207.14 |
| 4,915,691 | 4/1990 | Jones et al. | 604/73 |
| 5,000,175 | 3/1991 | Pue | 128/207.14 |
| 5,065,754 | 11/1991 | Jensen | 128/200.26 |
| 5,101,817 | 4/1992 | Etter | 128/200.26 |
| 5,325,851 | 7/1994 | Reynolds | 128/207.16 |
| 5,335,655 | 8/1994 | Kee | 128/207.16 |

*Primary Examiner*—Vincent Millin
*Assistant Examiner*—Eric P. Raciti
*Attorney, Agent, or Firm*—Lieberman & Nowak

[57] ABSTRACT

A method and apparatus is provided for aspiration of all patients, providing both a rigid suction hollow tube and a flexible suction hollow tube. The apparatus also include a ventilation adapter and a detachable tube for suctioning of liquid and particulate matter, such as meconium, and for intubation. Accordingly, oropharyngeal and nasopharyngeal suctioning of fluids and particulate matter is possible, as well as instillation of fluids and suctioning of the lower passageways, esophagus and stomach. The apparatus also includes a projecting appendage forming an oblique angle with the device, as an inlet port for delivery of oxygen or negative pressure and which can also function as a hook for conveniently hanging the device on a nearby edge.

27 Claims, 3 Drawing Sheets

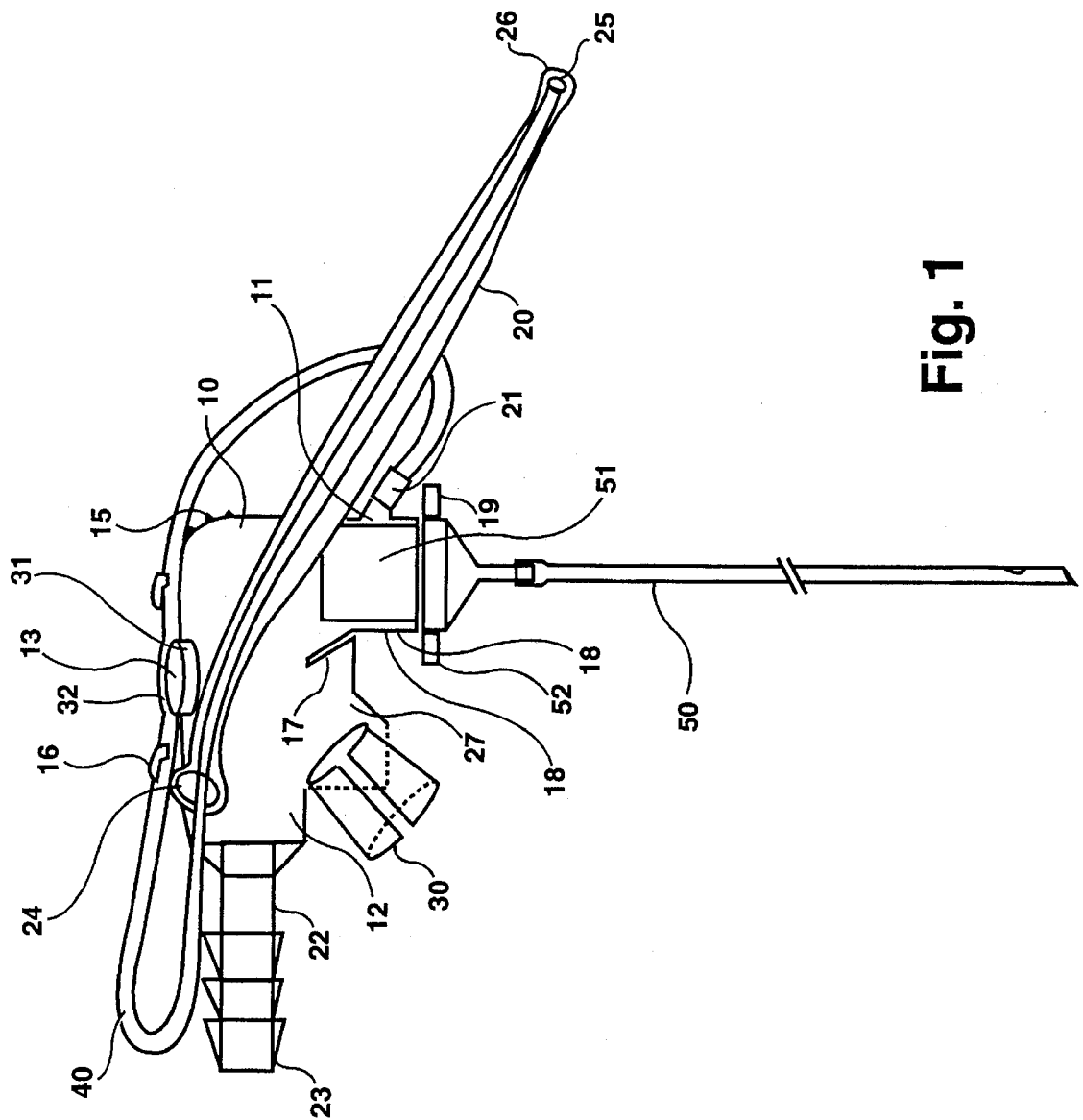

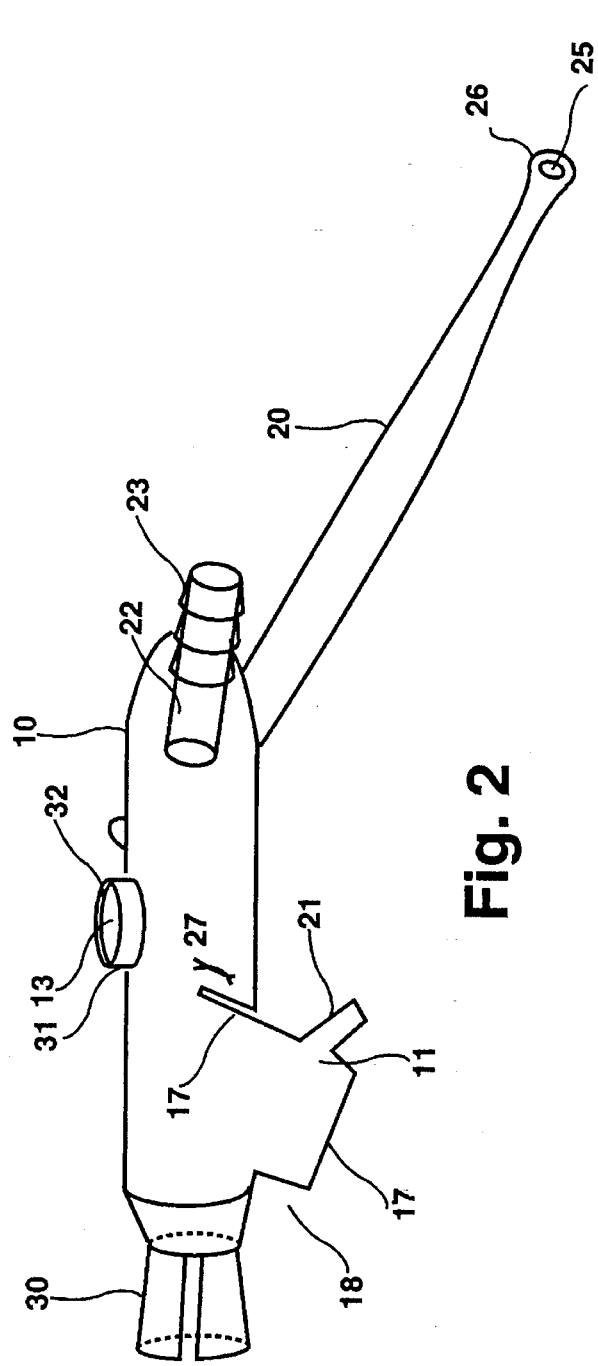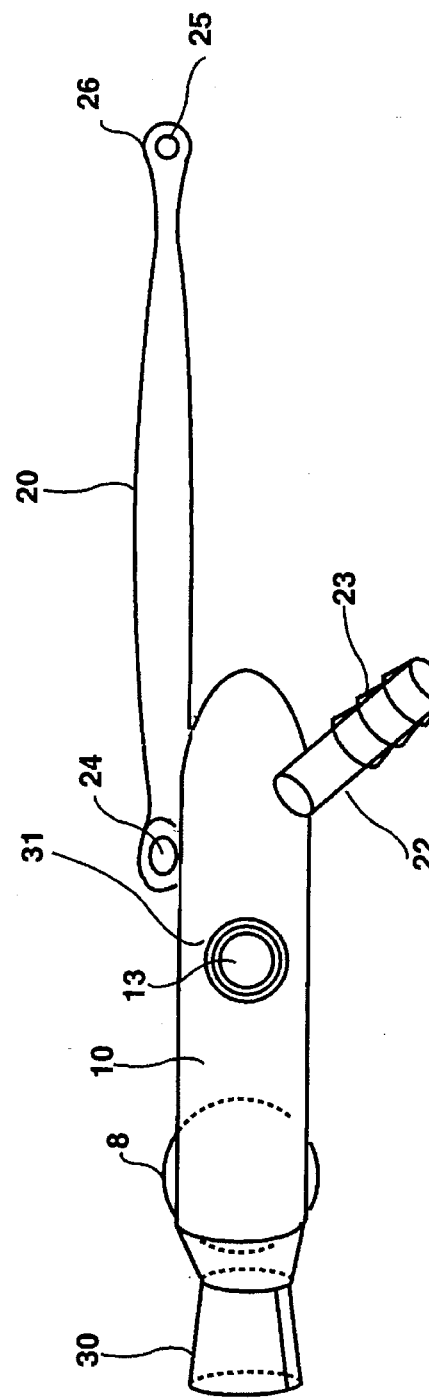

METHOD AND APPARATUS FOR VENTILATION AND ASPIRATION

FIELD OF THE INVENTION

The present invention relates generally to the field of aspiration, ventilation and instillation of fluids, in patients.

BACKGROUND OF THE INVENTION

It is often necessary to aspirate a patient to remove fluids and/or particles. Suction can be applied to maintain a patient's airway, and it can also be used to remove fluids from a surgical site. The area to be suctioned may be easily accessible through a large orifice or it may be in a hard to reach deep recess. Various suction equipment is available to meet the particular demands of the different situations requiring patient aspiration.

Neonates present one situation in which patient aspiration is, in various degrees, a routine practice. Since neonates, almost immediately upon delivery, change from being dependent on placental oxygen delivered through the umbilical vein, to room air oxygen inspired into the lungs, their oropharynx and nasopharynx must be suctioned to ensure the patency of these passageways and to prevent inhalation of fluid and/or particles located therein. Nasal suctioning is of particular importance in neonates as they are known to be obligate nasal breathers. A long thin flexible catheter is often used for suctioning newborns because of the ability to go both short distances into the nares and mouth as well as going beyond the nasopharynx and oropharynx, into the esophagus and stomach, to remove swallowed secretions. The ability to suction the esophagus and stomach is important because secretions located therein may be regurgitated and subsequently inhaled into the trachea and lungs.

Although simple and useful, control of the flexible catheter is limited, especially when suctioning in small oral cavities. The flexible catheter often requires use of both hands: one to direct the distal end of the catheter tip, the other to manipulate the suction port at the proximal end. Even when one attempts to operate the flexible catheter with one hand, a second hand is necessary to gather the catheter, position it at an optimal length, stabilize the length of the catheter, control the suction port and maintain the integrity of the suction system's connection. Since in the context of patient aspiration a free hand is often required to perform other functions— such as monitoring umbilical pulse rate, stabilizing and positioning the head, stabilizing the body, opening the jaw, handling equipment, drying the baby, and/or administering oxygen— the use of a flexible catheter can impair the patient care effort.

Accordingly in larger patients and other instances where the cavity to be suctioned is sufficiently large, the flexible catheter is often replaced with a rigid catheter, which provides more control. One common example of a rigid catheter is the Yankauer. However, some of the benefits associated with the flexible catheter, such as nasopharyngeal suction and entrance into irregular spaces, a common demand during surgical procedures, are lost when using a rigid catheter.

It is apparent that, in many situations, use of both the rigid catheter and the flexible catheter is advantageous. Yet, using two catheters entails multiple, time-consuming steps, especially if only one suction source is used, including: connecting the first suction catheter, performing the first function, detaching the first suction catheter, attaching the second catheter, and performing the second function. In addition, this procedure disrupts the flow of the aspiration effort and requires use of hand resources which could be performing other vital functions. This problem occurs during resuscitation, as well as during routine procedures such as suctioning a patient on a ventilator or suctioning body cavities during surgical procedures.

It is therefore, a principle objective of the present invention to provide a single device which functions as both a flexible and a rigid catheter. In its most rudimentary form, a flexible catheter and a rigid catheter whose distal and proximal ends are open, are connected side by side. The flexible catheter is attachable to a source of negative pressure and can be used as an ordinary flexible suction device when so desired. If a rigid suction device is indicated, the flexible catheter is inserted through the proximal open end of the rigid catheter, thereby causing the flow of negative pressure to exit through the distill open end of the rigid catheter.

As stated above, aspiration is a routine part of the delivery of neonates. In addition to the amniotic fluid that has to be removed from the neonatal's oropharynx and nasopharynx approximately ten percent (10%) of all neonates present with meconium in their airway, as well. Since inhaling the particulate matter of meconium can lead to hypoxia, acidosis, and a chemical pneumonitis, which in turn may result in severe morbidity or death, the presence of meconium is considered an emergency and the meconium fluid is often removed from the oropharynx intrapartum, by the obstetrician, as the baby's head is delivered. The baby is immediately intubated and suctioned to retrieve any aspirated meconium prior to the first breath of the infant, which would draw the meconium down into the lungs.

The situation is very tense as a skilled provider must use many pieces of equipment to rapidly intubate and suction either a limp, blue, non-breathing baby or a more active thrashing baby, before its first breath. To intubate, the operator must secure the head and body of the baby, position the head properly, retrieve and open a laryngoscope, open the baby's mouth, maintain its patency, insert the laryngoscope, locate, position and visualize the vocal cords to properly introduce an endotracheal ("ET") tube, find and properly grasp an ET tube, maintain visual contact with the vocal cords while introducing the ET tube into the oropharynx, introduce the ET tube, stabilize the ET tube, remove the stylet from within the lumen of the ET tube, attach the aspirator to the ET tube and suction. If necessary, this procedure is repeated until the baby is properly intubated.

Moreover, when the meconium is located above the vocal cords in the hypopharanyx, obstructing the line of sight to the vocal cords, the resuscitation effort becomes more difficult and the possibility of inhaling the meconium increases. While the objective, to place an ET tube into the trachea and apply negative pressure to aspirate any meconium is straightforward, it can be difficult due to the many factors affecting its success. Since each second delays the initiation of breathing and prolongs the hypoxia of the infant and secondary acidosis, time is of the essence.

It will be readily apparent to anyone skilled in the art that these difficulties are not peculiar to neonatal delivery. For example, with slight differences, emergency medical personnel face similar problems both in the field and in the emergency room.

While it is recommended by the Neonatal Advanced Life Support ("NALS") guidelines that two people be in attendance at meconium deliveries, the presence of meconium often times remains unknown until the end of the delivery process or during a precipitous delivery in which the pediatric staff is called emergently and the process of intubation is performed by the first single person present who is qualified to intubate. Indeed, single-operator meconium intubation is not an uncommon occurrence. In this situation, the difficulties elaborated above are compounded by the fact that the single operator must engage both hands to manipulate the equipment transfer and operate the multiple devices. The operator must often break visual contact with the vocal cords, as well as release the laryngoscope. If the laryngoscope is released before the ET tube is securely inserted in the trachea, the entire intubation process must be repeated. The equipment commonly available, as well as the prior art disclosures in this field do not adequately provide an effective solution.

It is therefore a second principal objective of the present invention to provide a single device which incorporates nearly all the necessary equipment for ventilation, aspiration and instillation of fluids to reduce if not eliminate the various difficulties described above. Since the multiple pieces of equipment are replaced with a single device, fewer steps are required in the initial setup, the possible need for searching for lost or misplaced equipment, the anxiety and distraction associated with such searches, and the need to maintain the juxtaposition and orientation of additional equipment, as well as the potential for entropy and chaos is decreased.

This single device includes a first inlet port for suctioning particulate matter such as meconium and a second inlet port for suctioning through a flexible or rigid catheter. The first inlet port has an inner diameter such that an ET tube adapter can be inserted therein and is situated relative to the second inlet port for the flexible or rigid catheter such that insertion of the ET tube adaptor through the first inlet port occludes the second inlet port. Accordingly, the flow of negative pressure can be alternately directed through the first inlet port and the second inlet port.

In addition since some situations requiring aspiration also require ventilation or application of positive pressure, the present invention also provides a novel port design that permits simultaneous attachment of a positive pressure source without removal of the endotracheal tube, thereby saving time and minimizing equipment. In neonatal resuscitation, this device would allow both suctioning and ventilation through the same ET tube, or suctioning and instillation, as for example, when performing a lung lavage as has been tried experimentally with surfactant. This novel port has dimensions to accommodate standard ventilation connectors as well as easy occlusion by a finger as would normally be necessary for flow control.

Other objectives of the present invention include a single resuscitation device with numerous finger grips and appendages for a more secure hold, especially desirable while wearing gloves; use of mechanical suction rather than poorly regulated mouth suction; and a single aspiration ventilation and instillation device attached to a non-interfering standard ET tube. Another objective of the present invention relates to the devices described above and suction devices in general. The difficulties in aspirating patients as described above, are complicated by the dangling hoses which connect ventilation and aspiration attachable devices to sources of oxygen and negative pressure, respectively. These hoses interfere with the operation and transfer of the attachable device by obstructing the line of sight and by projecting back toward the operator of the device, inhibiting free movement. An improved connecting appendage is described with an open proximal end extending from the attachable device toward the distal end and lateral side of the device forming an oblique angle with the attachable device. Thus, the connecting hose is directed away from the device, minimizing interference with the operator.

In addition, the oblique angle formed between the connecting appendage and the attachable device functions as a hook so that the device can conveniently hang from a stretcher, tray or other nearby edge. This helps to prevent potential slippage onto the ground, caused by the weight of the connecting hose to the relative lightweight device and maintains the device within hygienic domains and the operators immediate field of use, providing easier access.

Several prior art devices in the field of aspiration and ventilation follow: U.S. Pat. Nos. 4,699,138 ("'138") and 4,787,894 ("'894") provide an ET tube which can be used to suction and intubate the oropharynx simultaneously. Several problems are associated with these devices. First, the presence of the stylet in the ET tube of the '138 device, and the rigid wire embedded between the walls of the '894 device obstructs the suction flow for large of meconium particulate. While, in the '138 device, it is possible to remove the stylet, it requires the use of a second hand, forcing a single operator to release the laryngoscope. As explained above, this prolongs the intubation process and wastes precious time. Second, there is no teaching and presumably the device is incapable of, nasopharynx suctioning. Third, since a single channel is used for suctioning, the device does not provide a means to differentiate between meconium removed from the trachea and meconium removed from the oropharynx. The origin of the meconium is an important consideration for deciding whether further suctioning is indicated prior to ventilation.

Other prior art devices are disclosed in U.S. Pat. Nos. 4,275,724 ("'724"), 4,915,691 ("'691") and 5,000,175 ("'175"). The differences as well as the advantages of the present invention over these prior art devices will become apparent as the invention is described below.

SUMMARY OF INVENTION

One embodiment of the present invention is a single suction device attachable to a source of negative pressure, comprising a flexible catheter and a rigid catheter, such that when operated as described below, the functions of both a flexible and a rigid suction catheter are available in one unit. In addition, the flexible catheter may be detachable so that it can be used for instillation or removal of matter into or from the patient.

A second embodiment of the present invention is a single device capable of the dual suction functions described above, as well as having an inlet port into which a standard ET tube can be inserted and through which suctioning of particulate matter, such as meconium is possible. Insertion of the ET tube or an ET tube adapter directs the flow of negative pressure away from the flexible and rigid catheters and through the ET tube or adapter. This second embodiment can also be outfitted with an ET tube grasper so that the location of the ET tube is always known and is conveniently available for immediate use. The finger flow control valve commonly found on most suction devices is modified in this second embodiment to serve the added function of an inlet port for a ventilation device.

In either of the two embodiments, the detached flexible catheter can be used as a nasogastric tube ("NG") for the instillation and removal of fluids, gases and solids for gastric lavage, lung lavage, and emergency instillation of medications into the endotracheal tube such as epinephrine, naloxone or surfactant.

Both the first and second embodiments of the present invention may include a novel appendage serving as an inlet port for positive or negative pressure delivered through a tube connected to the device, from an external source. This appendage has a distal open end suitable for attachment to a standard hose used for the delivery of positive or negative pressure. The appendage extends from the body of the device, away from and toward the distal end of the device such that an oblique angle is formed between the appendage and the device. Accordingly, a hose connected to the device is directed away from the operator of the device, minimizing entangling and other interference. The oblique angle formed by the appendage and the device is also capable of functioning as a hook so that the device can hang from a nearby edge so that it is at all times conveniently located near the operator.

BRIEF DESCRIPTION OF THE DRAWINGS

FIG. 1 depicts one embodiment of the present invention, comprising a flexible catheter, rigid holster, endotracheal tube gripper, catheter restraints, flow control valve, fluid trap, and negative pressure source attachment means connected to a wand, to form a single device. FIG. 1 also depicts use of the present invention with an endotracheal tube, and its intersection with port 11 to form a novel valve for directing suction from the flexible catheter 10 to the endotracheal tube 50 or adaptor 51.

FIG. 2 depicts another embodiment of the present invention, modified to include an inlet source for delivery of negative pressure, projecting from the wand to form an oblique angle with the device.

FIG. 3 depicts an arial view of the same embodiment as shown in FIG. 2.

DETAILED DESCRIPTION OF THE INVENTION

Figure 4:
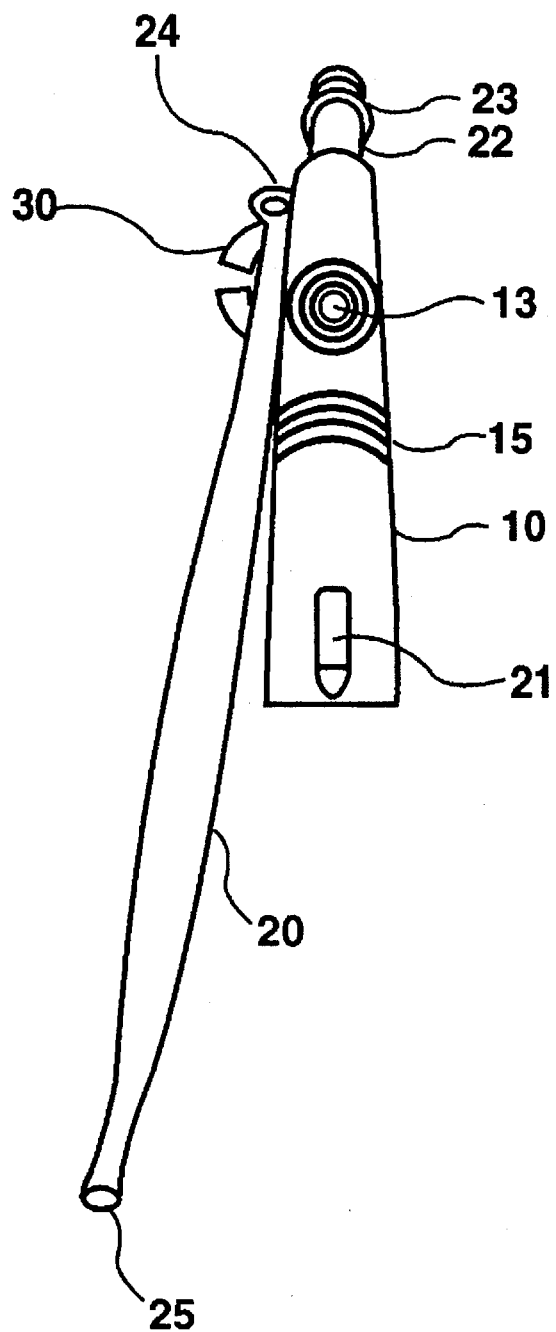
FIG. 4 depicts a frontal view of the embodiment as shown in FIG. 1.

Referring to FIG. 1, wand 10 has four ports. Distal port 11 opens to hollow appendage 21 which extends in a downward projection, forming an obtuse angle, preferably in the range of 120 to 150 degrees, with the wall of wand 10 immediately above appendage 21. The lower region between appendage 21 and wand 10 provides a finger rest for the operator. Proximal port 12 is the inlet port for a flow of negative pressure. Attachment means 22 may be permanently secured to port 12 for readily connecting wand 10 to a source of negative pressure. A conventional attachment means is depicted in FIG. 1, fitted with barbs 23, for a secured connection to a source of negative pressure.

Upper port 13 functions as a finger-operated flow control valve when wand 10 is connected to a source of negative pressure and as an inlet port for a ventilating device, when negative pressure is discontinued. A first cylindrical wall 32 extends above wand 10 from the edge of upper port 13. A second cylindrical wall 31 also extends above wand 10, surrounding the first cylindrical wall 32. Second cylindrical wall 31 has a diameter such that a standard ventilating source can be securely coupled thereon. Alternatively, cylindrical wall 31 can be constructed with an inner diameter suitable for occlusion with the operator's finger, and an outer diameter suitable for connecting to a standard ventilating source. This obviates the need for cylindrical wall 32. As referred to herein, ventilating sources refer to, for example, resuscitation bags and mechanical ventilators.

Lower port 19 is the outlet for either the negative or positive pressure connected to wand 10 and has a diameter such that a standard endotracheal ("ET") tube 50 can be securely attached thereto by insertion of the ET adapter 51.

One preferred means of securely attaching ET adapter 51 to wand 10 is for wand 10 to extend to form a tapered hollow cylindrical tube 18 ending at port 19.

Insertion of ET adapter 51 through lower port 19 and into the cylindrical tube 18 will occlude distal port 11. The externally delivered negative pressure or oxygen can thus be instantaneously diverted away from the flexible suction catheter, to the ET tube adapter 51 for suctioning liquid and particulate material such as meconium.

It should be readily apparent to one skilled in the art that for any of the embodiments of the present invention, all ports other than the inlet and outlet ports for negative pressure, must be sealed for suction to be possible.

A flexible hollow tube 40, such as a flexible catheter conventionally used for patient aspiration or instillation, is connected to appendage 21 by inserting the distal end of appendage 21, through the proximal opening of flexible hollow tube 40. The connection of appendage 21 to flexible hollow tube 40 may be designed to enable easy and quick attachment and detachment.

A rigid hollow tube 20 such as a rigid catheter conventionally used for patient aspiration, is attached along the outer wall of one side of wand 10 such that rigid hollow tube 20 projects from wand 10. The inner diameter of first opening 24 is greater than the outer diameter of flexible hollow tube 40 so that flexible hollow tube 40 can be easily inserted into first opening 24. Rigid tube 20 has a tapered lumen so that the diameter decreases from opening 24 to opening 25. Distal end 26 of rigid tube 20 forms a rounded edge to reduce the possibility of trauma when inserted into a patient's oropharynx.

The lumen of rigid hollow tube 20 preferably has a curvature in the range of 30–60 degrees such that flexible hollow tube 40, when inserted through first opening 24 will be directed in a downward fashion to second opening 25.

The length of rigid hollow tube 20 is consistent with the size of the area to be suctioned. For example, if the oropharynx of a neonate were to be suctioned, its length should be long enough to extend to the posterior aspect of the oropharynx (25) and extend slightly beyond the patient's lips.

One embodiment of the present invention is a device having a rigid catheter, such as rigid hollow tube 20, attached to a flexible catheter, such as flexible hollow tube 40, operating together as described above. A finger flow control valve, similar to port 13 in FIGS. 1, 2 and 3 can also be included for better flow regulation. In this embodiment, an attachment means to a source of negative pressure is included, however, there is no need to provide a means for attachment to a ventilating source. A conventional attachment means can be used, as depicted in FIG. I or an improved attachment means can be used, as depicted in FIGS. 2 and 3 and described in more detail below.

A second embodiment of the present invention includes appendage 21 having a length suitable for operation as a rigid catheter. When it is determined that suction through a rigid catheter is indicated, flexible hollow tube 40 can be detached from appendage 21. Appendage 21 can then be inserted directly into the patient's airway or other suction site. This obviates the need for rigid hollow tube 20.

Multiple restraints 16 are attached to the outer wall of wand 10, having a curved or circular configuration such that flexible tube 40 can be positioned therein, preventing flexible hollow tube 40 from interfering with vision or balance of the device when it is inserted in rigid hollow tube 20. One preferred embodiment includes two such restraints.

Wand 10 also includes various gripping attachments to allow easier control in the operator's hands. This is especially necessary as the device will often be used in situations such as meconium deliveries in which a large amount of slippery secretions such as meconium, amniotic fluid and blood are present. Although the device of the present invention can be used with bare hands, universal precautions and barrier protection with gloves is strongly recommended. Since gloves, often latex, may make manipulations more difficult, the gripping attachments, the finger rest, formed by the appendage 21 and the cylindrical wall 18, the finger rest formed by fluid trap 27 and any other finger rests formed by variations in the shape of the device that are within the scope of the claimed invention, as well as the gripping ridges 15 on the outer upper surface of wand 10 are included in the device.

The lower inner surface of wand 10 may include an oblique ridge 17, which forms a wall extending within wand 10, angled toward the upper region of wand 10. This wall forms a division between the anterior section of wand 10, encompassing distal port 11 and the lower port 19, and the posterior section of wand 10. The posterior section of wand 10 below the upper edge of ridge 17 forms a depression 27, providing a fluid trap for material suctioned from lower port 14. The fluid trap enables the operator of the device to determine the amount of material suctioned, and at what point in the procedure this had been done. The fluid trap 27 and oblique ridge 17 prevent the backflow of suctioned material.

Wand 10 is preferably made of a transparent material to further assist the operator to ascertain that the device is functioning and to allow for visual analysis of the results of the procedure.

A gripping attachment 30 projects from alongside wand 10. As depicted in FIGS. 1, 2 and 3, gripping attachment 30 forms an incomplete cylinder, such that a slit runs along its entire length. The slit enables the insertion of an endotracheal tube adapter 51, without interference of the winged extensions 52 or a stylet which might be preferentially placed through adapter 51 and endotracheal tube 50. Other suitable devices such as clips or clamps, will be readily apparent to those skilled in the relevant art.

Another embodiment of the present invention is depicted in FIGS. 2 and 3. The device has a uniquely positioned inlet port for delivery of negative pressure. In this embodiment distal port 11 is relocated alongside wand 10. Attachment means 22 projects from wand 10 forming an oblique angle with wand 10. In one preferred embodiment, attachment means 22 forms a 45 degree angle with wand 10. Situating attachment means 22 as depicted in FIGS. 3 and 4 minimizes interference between the hose connecting the device to an external source of negative pressure and the operator, by directing the connecting hose away from the device and operator. The oblique angle also forms a hook for hanging the device from a nearby edge.

To some extent, the instant invention has been described as it relates to neonatal resuscitation as this is a most complex procedure requiring all of the innovations and specifications of the preferred embodiment of the instant invention. This should not be construed to exclude application of the present invention under other circumstances which employ the device to a more limited degree or with altered dimensions. It will be readily apparent to one of ordinary skill in the art that the present invention has many other applications consistent with its design.

What is claimed is:

1. A suction device comprising:

a flexible hollow tube having a distal open end and a proximal end, said proximal end including means for connecting said flexible hollow tube to a source of negative pressure, to form a path of negative pressure between it source of negative pressure and said distal open end;

a rigid hollow tube attachable to said flexible hollow tube having distal and proximal open ends, said rigid hollow tube having an inner diameter such that said distal open end of said flexible hollow tube can be inserted through said proximal open end to said distal of said rigid hollow tube; and means for attaching said rigid hollow tube to said flexible hollow tube so as not to obstruct said proximal or distal ends of each of said flexible and rigid tubes, and such that said flexible and rigid hollow tubes can be separated.

2. A device according to claim 1 wherein an orifice is situated on said suction device along said path of negative pressure, having an inner diameter such that an operator of said Suction device can cover said orifice with a finger thereby controlling said flow of negative pressure at said distal end of said flexible hollow tube.

3. A device according to claim 1 having gripping means for securely holding a conventional endotracheal tube when said endotracheal tube is not in use, and from which endotracheal tube is easily detached when its use is desired.

4. A method for suctioning including use of a flexible hollow tube having a distal open end and a proximal end and a rigid hollow tube having distal and proximal open ends, said rigid hollow tube having an inner diameter such that said distal open end of said flexible hollow tube can be inserted through said proximal open end of said rigid hollow tube, the method comprising the steps of:

releasably connecting said flexible hollow tube to said rigid hollow tube, attaching said flexible hollow tube to a source of negative pressure, inserting said distal open end of said flexible hollow tube into a site to be suctioned, determining whether a procedure requires the use of said rigid hollow tube for suctioning, and inserting said distal open end of said flexible hollow tube into said proximal open end of said rigid hollow tube when it is determined that said procedure requires the use of said rigid hollow tube.

5. A method for suctioning fluids and particulate matter prior and subsequent to endotracheal intubation, including use of a flexible hollow tube having distal and proximal open ends, and a wand having a cavity, a plurality of ports, a hollow cylindrical appendage projecting from a first port, a second port situated generally below said first port having an inner diameter suitable for inserting a standard endotracheal tube adapter such that said endotracheal tube adapter will occlude said first port, comprising the steps of:

releasably connecting said proximal open end of said flexible hollow tube to said hollow cylindrical appendage;

attaching said wand to a source of negative pressure via a third inlet port;

inserting said distal open end of said flexible hollow tube into a site to be suctioned;

determining whether a procedure requires the use of said endotracheal tube adaptor; and inserting said endotracheal tube adapter through said second hole, thereby occluding the flow of suction through said flexible hollow tube, directing suction through said endotracheal tube adaptor when it is determined that said procedure requires the use of said endotracheal tube adaptor.

6. A method for suctioning fluids and particulate matter prior and subsequent to endotracheal intubation, including use of a wand having a cavity and a plurality of ports, a hollow cylindrical appendage projecting from a first port and having a distal open end, a second port situated generally below said first port having an inner diameter suitable for inserting a standard endotracheal tube adaptor such that said endotracheal tube adaptor will occlude said first port, comprising the steps of:

attaching said wand to a source of negative pressure via a third inlet port;

inserting said distal open end of said hollow cylindrical appendage into a site to be suctioned;

determining whether a procedure requires use of said endotracheal tube adaptor; and inserting said endotracheal tube adaptor through said second hole, thereby occluding the flow of suction through said hollow cylindrical appendage, directing suction through said endotracheal tube adaptor when it is determined that said procedure requires the use of said endotracheal tube adaptor.

7. A device for suctioning fluids and particulate matter prior and subsequent to endotracheal intubation, comprising:

a wand having a cavity and an outer surface defining upper, lower, distal and proximal regions which further define a flow passageway, and having a plurality of ports;

a hollow, cylindrical appendage projecting from a first port located at the surface of said wand;

a flexible hollow tube attachable to said hollow, cylindrical appendage;

a second port at the surface of said wand, situated generally below said first port, said second port having an inner diameter suitable for inserting a standard endotracheal tube adaptor, such that said endotracheal tube adaptor will occlude said first port directing all flow away from said first port and through said second port; and a third inlet port for connecting said wand to a source of negative pressure.

8. A device according to claim 7 wherein a fourth port is located at the outer upper surface of said wand, said fourth port having an edge which extends above the outer surface of said wand, forming a cylindrical wall around said fourth port having an upper end whose inner diameter is capable of being sealed by a person's finger.

9. A device according to claim 7 wherein a fourth port is located at said outer upper surface of said wand, said fourth port having an edge that extends above said outer surface of said wand, forming a first cylindrical wall around said fourth port having an upper end whose outer diameter is capable of being sealed by a person's finger, said cylindrical wall surrounded by a second cylindrical wall that extends above said outer surface of said wand, having an upper edge whose outer diameter is suitable for attachment to a standard ventilating device.

10. A device according to claim 7 wherein a fourth port is located at the outer upper surface of said wand, said fourth port having an edge which extends above the outer surface of said wand, forming a cylindrical wall around said fourth port having an upper end whose inner diameter is capable of being sealed by a person's finger, and whose outer diameter is suitable for attachment to a standard ventilating device.

11. A device according to claim 6 wherein said second port has an edge which extends downward from the outer surface of said wand forming a cylindrical wall having a lower open end and a tapered inner diameter such that a conventional endotracheal tube adapter can be inserted therein, and the inner diameter at the lower open end being larger than the inner diameter of said second port.

12. A device according to claim 6 wherein multiple restraints are attached to the outer surface of said wand suitable to restrain said flexible tube.

13. A device according to claim 7 wherein an oblique ridge within said cavity of said wand, extends from the edge of the second port such that a trap region is formed between said ridge and the lower region of said wand, preventing backflow of any material suctioned into said wand.

14. A device according to claim 7 having a rigid hollow tube attachable to said device having distal and proximal open ends such that said flexible hollow tube can be inserted through said proximal open end of said rigid hollow tube.

15. A device according to claim 7 wherein a gripping means is attached to said outer surface of said wand for securely holding a conventional endotracheal tube adapter and from which said adapter can be easily attached and detached.

16. A device according to claim 7 wherein said outer surface of said wand is designed such that the frictional coefficient of said wand is increased in selected places so that said wand can be more securely grasped by its operator.

17. A device according to claim 7 wherein a conventional coupling appendage for connecting to a source of negative pressure extends from said third inlet port.

18. A device for suctioning fluids and particulate matter prior and subsequent to endotracheal intubation, comprising:

a wand having a cavity and an outer surface defining upper, lower, distal and proximal regions which further define a flow passageway, and having a plurality of ports;

a hollow, cylindrical appendage projecting from a first port located at the surface of said wand;

a second port at the surface of said wand, situated generally below said first port, said second port having an inner diameter suitable for inserting a standard endotracheal tube adaptor, such that said endotracheal tube adaptor will occlude said first port directing all flow away from said first port and through said second port; and a third inlet port for connecting said wand to a source of negative pressure.

19. A device according to claim 18 wherein a conventional coupling appendage for connecting to a source of negative pressure extends from said third inlet port.

20. A device according to claim 18 wherein a fourth port is located at the outer upper surface of said wand, said fourth port having an edge which extends above the outer surface of said wand, forming a cylindrical wall around said fourth port having an upper end whose inner diameter is capable of being sealed by a person's finger.

21. A device according to claim 18 wherein a fourth port is located at said outer upper surface of said wand, said fourth port having an edge that extends above said outer surface of said wand, forming a first cylindrical wall around said fourth port having an upper end whose outer diameter is capable of being sealed by a person's finger, said cylindrical wall surrounded by a second cylindrical wall that extends above said outer surface of said wand, having an upper edge whose outer diameter is suitable for attachment to a standard ventilating device.

22. A device according to claim 18 wherein a fourth port is located at the outer upper surface of said wand, said fourth port having an edge which extends above the outer surface of said wand, forming a cylindrical wall around said fourth port having an upper end whose inner diameter is capable of being sealed by a person's finger, and whose outer diameter is suitable for attachment to a standard ventilating device.

23. A device according to claim 18 wherein the edge of said second port extends downward from the outer surface of said wand forming a cylindrical wall having a lower open end and a tapered inner diameter such that a conventional endotracheal tube adapter can be inserted therein, and the inner diameter at the lower open end being larger than the inner diameter of said second port.

24. A device according to claim 18 wherein multiple appendages are attached to the outer surface of said wand suitable to restrain said flexible tube.

25. A device according to claim 18 wherein an oblique ridge within said cavity of said wand, extends from the edge of the second port such that a trap region is formed between said ridge and the lower region of said wand, preventing backflow of any material suctioned into said wand.

26. A device according to claim 18 wherein a gripping means is attached to said outer surface of said wand for securely holding a conventional endotracheal tube adapter and from which said adapter can be easily attached and detached.

27. A device according to claim 18 wherein said outer surface of said wand is designed such that the frictional coefficient of said wand is increased in selected places so that said wand can be more securely grasped by its operator.

* * * * *

UNITED STATES PATENT AND TRADEMARK OFFICE
CERTIFICATE OF CORRECTION

PATENT NO. : 5,562,077
DATED : October 8, 1996
INVENTOR(S) : Joseph Schultz It is certified that error appears in the above-identified patent and that said Letters Patent is hereby corrected as shown below:

At Colum 10, line 8, please delete "6" and insert --7-- therefore

At Column 10, line 15, please delete "6" and insert --7-- therefore

Signed and Sealed this

Sixth Day of January, 1998

Attest:

BRUCE LEHMAN

Attesting Officer     Commissioner of Patents and Trademarks

REEXAMINATION CERTIFICATE (4148th)

United States Patent [19]

Schultz

[11] B1 5,562,077
[45] Certificate Issued Sep. 5, 2000

[54] METHOD AND APPARATUS FOR VENTILATION AND ASPIRATION

[75] Inventor: Joseph Schultz, 564 First Ave., Apt. 21-R, New York, N.Y. 10016

[73] Assignee: Joseph Schultz, Phoenix, Ariz.

Reexamination Request:
No. 90/005,229, Jan. 22, 1999

Reexamination Certificate for:
Patent No.: 5,562,077
Issued: Oct. 8, 1996
Appl. No.: 08/416,304
Filed: Apr. 4, 1995

Certificate of Correction issued Jan. 6, 1998.

[51] Int. Cl.[7] .......... A61M 16/04; A61M 25/088
[52] U.S. Cl. .............. 128/207.14; 128/202.27; 604/35
[58] Field of Search .................. 604/317, 326, 604/327, 540, 902, 542

[56] References Cited

U.S. PATENT DOCUMENTS

| | | | |
|---|---|---|---|
| 3,902,494 | 9/1975 | Haberlen et al. | 604/902 |
| 4,451,257 | 5/1984 | Atchley | 604/902 |
| 4,729,765 | 3/1988 | Eckels et al. | 604/54 |
| 5,123,403 | 6/1992 | Lavyne | 604/902 |
| 5,279,549 | 1/1994 | Ranford | 604/902 |

FOREIGN PATENT DOCUMENTS

| 2142244 | 1/1985 | United Kingdom | 604/317 |
|---|---|---|---|

OTHER PUBLICATIONS

Neotech Meconium Aspirator Catalog N. N0101 Product Card Dated Apr. 1994.

*Primary Examiner*—John G. Weiss

[57] ABSTRACT

A method and apparatus is provided for aspiration of all patients, providing both a rigid suction hollow tube and a flexible suction hollow tube. The apparatus also include a ventilation adapter and a detachable tube for suctioning of liquid and particulate matter, such as meconium, and for intubation. Accordingly, oropharyngeal and nasopharyngeal suctioning of fluids and particulate matter is possible, as well as instillation of fluids and suctioning of the lower passageways, esophagus and stomach. The apparatus also includes a projecting appendage forming an oblique angle with the device, as an inlet port for delivery of oxygen or negative pressure and which can also function as a hook for conveniently hanging the device on a nearby edge.

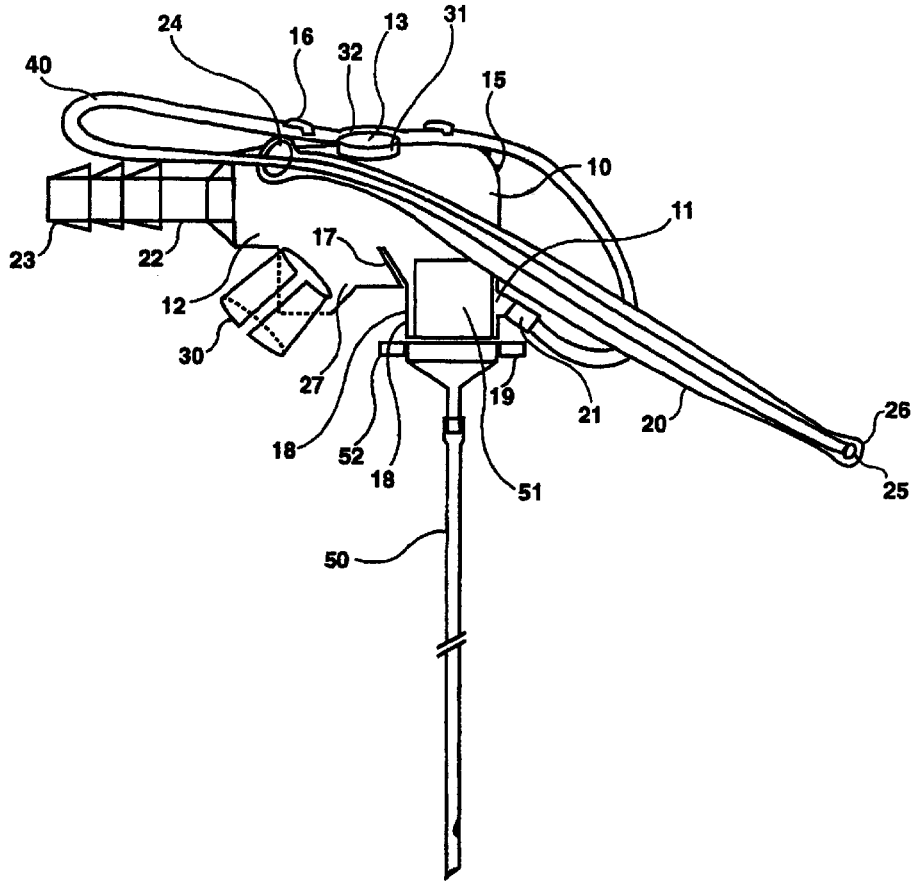

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 4–27 is confirmed.

Claim 1 is determined to be patentable as amended.

Claims 2 and 3, dependent on an amended claim, are determined to be patentable.

1. A suction device comprising:

a flexible hollow tube having a distal open end and a proximal end, said proximal end including means for connecting said flexible hollow tube to a source of negative pressure, to form a path of negative pressure between [it] *the* source of negative pressure and said distal open end;

a rigid hollow tube attachable to said flexible hollow tube having distal and proximal open ends, said rigid hollow tube having an inner diameter *larger than that of said flexible hollow tube* such that said distal open end of said flexible hollow tube can be *readily* inserted *and slid* through said proximal open end to said distal *end* of said rigid hollow tube; and means for attaching said rigid hollow tube to said flexible hollow tube so as not to obstruct said proximal or distal ends of each of said flexible and rigid tubes, and such that said flexible and rigid hollow tubes can be separated.

* * * * *